United States Patent [19]

Hazen et al.

[11] Patent Number: 4,603,227
[45] Date of Patent: Jul. 29, 1986

[54] NOVEL PROCESS FOR PREPARING α-(TRICHLOROMETHYL)BENZYL ALCOHOLS FROM BENZALDEHYDES

[75] Inventors: George G. Hazen, Perth Amboy; Jean M. Wyvratt, Mountainside, both of N.J.

[73] Assignee: Merck & Co., Inc., Rahway, N.J.

[21] Appl. No.: 780,135

[22] Filed: Sep. 25, 1985

[51] Int. Cl.$^4$ .............................................. C07C 33/46
[52] U.S. Cl. .................................................. 568/812
[58] Field of Search ......................................... 568/812

[56] References Cited

U.S. PATENT DOCUMENTS 3,419,623 12/1968 Nordin ................................. 568/812

OTHER PUBLICATIONS

Bal'on et al, "Zh. Obsch. Khim", vol. 44, p. 2633 (1974).
Atkins et al, "J. Chem. Soc.", Chem. Comm. (1983) pp. 283–284.

Primary Examiner—Werren B. Lone
Attorney, Agent, or Firm—Manfred Polk; David L. Rose; Michael C. Sudol, Jr.

[57] ABSTRACT

This invention relates to a novel and improved process for preparing α-(trichloromethyl) benzyl alcohols, particularly, trichloromethyl-3-nitrobenzyl alcohol a key intermediate useful in the preparation of clorsulon (4-amino-6-(trichloroethenyl)-1,3-benzene-disulfonamide) via a base-catalyzed condensation reaction of benzaldehydes and chloroform.

12 Claims, No Drawings

NOVEL PROCESS FOR PREPARING α-(TRICHLOROMETHYL)BENZYL ALCOHOLS FROM BENZALDEHYDES

BACKGROUND OF THE INVENTION

This invention relates to a novel and improved one-step process for preparing α-(trichloromethyl)carbinols via a base-catalyzed condensation reaction of benzaldehydes and chloroform. One of the compound prepared via this process, Trichloromethyl-3-nitrobenzyl alcohol is a key intermediate useful in the preparation of a class of anthelmintic disulfonamide compounds, in particular, the process for preparing 4-amino-6-(trichloroethenyl)-1,3-benzenedisulfonamide also referred to as clorsulon is disclosed in U.S. Pat. No. 4,500,736. The anthelmintic compounds referred to herein are disclosed in U.S. Pat. No. 4,064,239 and are particularly useful against liver fluke in sheep and cattle.

DESCRIPTION OF THE PRIOR ART

The condensation of chloroform with benzaldehydes under basic conditions is a standard method for the preparation of α-(trichloromethyl)benzyl alcohols, which serve as intermediates in a variety of synthetic applications. With highly reactive aldehydes, such as nitrobenzaldehydes, the competing Cannizzaro reaction is often a serious problem resulting in low yields or exclusively Cannizzaro products.

Several articles have described the condensation of substituted benzaldehyde derivatives with chloroform in the presence of various bases to produce the corresponding α-(trichloromethyl)benzyl alcohols. In the case of nitrosubstituted benzaldehydes, only Cannizzaro reaction products are obtained when powdered potassium hydroxide is used as the base without solvent. Phase transfer conditions produce a mixture of nitrobenzoic acid, nitrobenzyl alcohol, and trichloromethyl-nitrobenzyl alcohol. Potassium t-butoxide in liquid ammonia at −75° C. has been reported to effect the desired condensation to form trichloromethyl-3-nitrobenzyl alcohol in 72% yield (Ya. G. Bal'on, V. E. Paranyuk, and M. D. Shul'man, *Zh. Obsch. Khim.*, 44, 2633 (1974)). Under the same conditions potassium hydroxide or calcium oxide in dimethyl sulfoxide gives 5–10% lower yields. The generation of trichloromethide anion in solution from the decomposition of trichloroacetic acid in dimethyl sulfoxide has been used to prepare trichloromethyl-4-nitrobenzyl alcohol in 60% yield (P. J. Atkins et al., *J. Chem. Soc., Chem. Comm.*, 1983, pp. 283–4).

SUMMARY OF THE INVENTION

This invention relates to a novel and improved one step process for the preparation of α-(trichloromethyl)benzyl alcohols, particularly, trichloromethyl-3-nitrobenzyl alcohol, a key intermediate useful in the preparation of trichlorovinyl benzenedisulfonamide anthelmintic agents.

Accordingly, it is an object of this invention to provide a novel and improved one-step process for preparing trichloromethyl-3-nitrobenzyl alcohol.

A further object of this invention is to describe the specific reaction conditions and reagents which produce an unexpected yield of the key intermediate, trichloromethyl-3-nitrobenzyl alcohol.

Another object of this invention is to provide reaction conditions which eliminate the expected Cannizzaro reaction and provide an intermediate in an unexpected high yield without a decrease in product purity.

These and other objects of the invention will become apparent from the following description.

DESCRIPTION OF THE INVENTION

The α-(trichloromethyl)benzyl alcohol compounds prepared via this novel and improved one step process of this invention are represented by the general formula below:

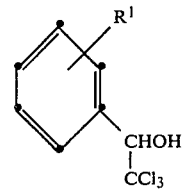

wherein $R_1$ is H; alkoxy($C_1$–$C_6$) such as methoxy, ethoxy, isopropoxy and the like; nitro; alkyl ($C_1$–$C_6$) such as methyl, isopropyl, hexyl and the like; halogen such as chloro, bromo and the like; amino; aryl ($C_6$–$C_9$) such as phenyl; and aralkyl such as benzyl($C_7$–$C_{12}$) and the like.

The invention concerns a novel and improved one-step base condensation process for the preparation of α-(trichloromethyl)carbinols, particularly, trichloromethyl-3-nitrobenzyl alcohol, an intermediate useful in the preparation of trichlorovinyl benzenedisulfonamide anthelmintic agents. The novel and improved one-step process disclosed herein involves a method for condensation of chloroform with aldehydes using an alkanol such as methanol, ethanol, isopropanol and the like, a base such as potassium hydroxide, sodium hydroxide, calcium hydroxide, sodium methoxide, potassium t-butoxide and the like in a dipolar-aprotic solvent such as dimethylformamide, N-methylpyrrolidinone, N-ethylpyrrolidinone and the like at sub-zero (approximately −25° C.) to 0° C. Using this procedure, trichloromethyl-3-nitrobenzyl alcohol is prepared in 90% isolated yield without Cannizzaro by-products. This method is also used to prepare α-(trichloromethyl) carbinols from benzaldehyde, 4-anisaldehyde, and the like.

In this invention we describe the preparation of trichloromethyl-3-nitrobenzyl alcohol in high yield with no detectable Cannizzaro product and demonstrate the generality of the method for the condensation of chloroform with other aldehydes and ketones. Initially, potassium fluoride supported on alumina was the base of choice for this condensation since the fluoride base would prevent the Cannizzaro side reaction. Characterization by infrared and Raman spectroscopy of this supported base showed the presence of potassium hexafluoroaluminate rather than potassium fluoride. Aqueous potassium fluoride had reacted with alumina to produce potassium hexafluoroaluminate and hydroxide. This observation prompted the use of potassium hydroxide supported on Super-Cel as the base to give TMBA in 93% isolated yield. The method described herein avoids the preparation and variable activity of the supported hydroxide base. A mixture of chloroform (2.25 equivalents) and 3-nitrobenzaldehyde (one equivalent) in dimethylformamide (DMF) at 0° C. was treated with a methanolic solution of potassium hydroxide (0.7 equivalents). After work-up, the desired alcohol TMBA was obtained in 98% yield and crystallized from toluene/hexane to give analytically pure trichloromethyl-3-nitrobenzyl alcohol in 90% yield.

The generality of this method for condensation of chloroform with carbonyl compounds was examined and the results are summarized in Table I below:

TABLE I

Yields of Trichloromethyl Carbinols

| Carbonyl Compound | Yield[a,b] | Product |
|---|---|---|
| 3-nitrobenzaldehyde | 90% | ethyl-3-nitrobenzyl alcohol |
| benzaldehyde | 99% | trichloromethylbenzyl alcohol |
| 4-anisaldehyde | 97% | trichloromethyl-4-methoxybenzyl alcohol |

[a] All products exhibited the expected $^1$H and $^{13}$C NMR and MS characteristics and gave satisfactory elemental analyses.
[b] Isolated yields after distillation or crystallization.

This method permits the preparation of a variety of α-trichloromethyl carbinols in high yield using the convenient potassium hydroxide base in methanol/DMF.

The following examples illustrate the novel and improved process of the invention and should be construed as an illustration rather than limitation thereof.

EXAMPLE I

Trichloromethyl-3-nitrobenzyl alcohol (TMBA)

To a solution of 3-nitrobenzaldehyde (200 g, 1.32 mol) and chloroform (238 ml, 2.97 mol) in 800 ml of DMF cooled to −9° C. under nitrogen was added dropwise a solution of potassium hydroxide (59.8 g, 0.92 mol) in 180 ml of methanol over a 2.7 hour period. The deep purple reaction mixture was aged for 2 hours at −8° C. before quenching over 40 minutes into 1.8 liter of 1N HCl and 1.8 liter of toluene cooled to −5° C. The quench mixture was stirred and cooled for an additional 0.5 hour and then brought to ambient temperature. The toluene layer was separated and washed twice with 1.8 liter of water. After treatment with 35 g of Darco G-60 charcoal for 1 hour and filtration through Super-Cel, the organic layer was washed with 1.8 liter of aqueous 5% sodium bicarbonate solution and then 1.8 liter of water. After evaporation to 550 ml the desired product was crystallized by the addition of 450 ml of hexanes. The resulting slurry was cooled at 0° C. for 2 hours and the solid was collected by filtration and rinsed with hexanes. After drying, 320 g (90% yield) of TMBA was obtained; m.p. 91–95° C; $^1$H NMR 3.75 (1H, d, J=1 Hz), 5.25 (1H, d, J=1 Hz), 7.20–8.45 (5H, m).

Anal. Calc'd for $C_8H_6NO_3Cl_3$:
C, 35.52; H, 2.24; N, 5.18; Cl, 39.32.
Found: C, 35.78; H, 2.23; N, 5.34; Cl, 39.38.

EXAMPLE II

When N-methylpyrrolidinone or N-ethylpyrrolidinone; sodium hydroxide, potassium t-butoxide, calcium hydroxide or sodium methoxide; ethanol or isopropanol are substituted for dimethylformamide, potassium hydroxide and methanol, respectively, under the same reaction conditions employed in Example I, there is obtained trichloromethyl-3-nitrobenzyl alcohol.

EXAMPLE III

Following the procedure of Example I and substituting benzaldehyde, 4-anisaldehyde and other starting material compounds and substituting the reagents of Example II, there is obtained trichloromethylbenzyl alcohol, trichloromethyl-4-methoxybenzyl alcohol and the benzaldehyde corresponding to said starting material compound, respectively.

EXAMPLE IV

Trichloromethyl-3-nitrobenzyl alcohol (TMBA)

To a solution of 3-nitrobenzaldehyde (80 g, 0.53 mol) and chloroform (95 ml, 1.17 mol) in 320 ml of N-methylpyrrolidinone cooled to −10° C. under nitrogen was added dropwise a solution of potassium hydroxide (24 g, 0.43 mol) in 80 ml of methanol over a 40 minute period. The deep purple reaction mixture was aged for 4 hours at −5° C. before quenching into 640 ml of 1N HCl and 500 ml of methylene chloride cooled to 0° C. The quench mixture was stirred and cooled for an additional 0.5 hour and then brought to ambient temperature. The methylene chloride layer was separated and washed twice with 720 ml of water, 720 ml of 10% sodium bisulfite, and again with 720 ml of water. After treatment with 9.0 g of Darco G-60 charcoal for 1 hour and filtration through Super-Cel, the organic layer was washed with 450 ml of aqueous 5% sodium bicarbonate solution and then 720 ml of water, with 65 ml of saturated salt solution added. The resulting methylene chloride solution contained 140.2 g (98.4% yield) of TMBA.

What is claimed is:

1. A process for preparing α-(trichloromethyl)benzyl alcohols of the formula

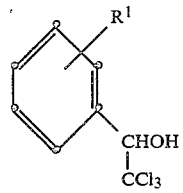

wherein $R_1$ is hydrogen, alkoxy ($C_1$–$C_6$), nitro, alkyl($C_1$–$C_6$), halogen, amino, aryl($C_6$–$C_9$) or aralkyl ($C_7$–$C_{12}$) which comprises condensing a benzaldehyde compound with chloroform in the presence of a dipolar-aprotic solvent and a base in an alkanol at a sub-zero to zero degree temperature.

2. The process of claim 1, wherein said benzaldehyde compound is selected from the group consisting of 3-nitrobenzaldehyde, benzaldehyde and 4-anisaldehyde; said dipolar-aprotic solvent is selected from the group consisting of dimethylformamide, N-methylpyrrolidinone and N-ethylpyrrolidinone; said base is selected from the group consisting of sodium hydroxide, potassium t-butoxide, calcium hydroxide, sodium methoxide and potassium hydroxide; and said alkanol is selected from the group consisting of methanol, ethanol and isopropanol at temperature ranging from −25° C. to 0° C.

3. The process of claim 2, wherein said compound is 3-nitrobenzaldehyde, said solvent is dimethylformamide, said base is potassium hydroxide and said alkanol is methanol at temperatures ranging from −15° to 0° C.

4. The process of claim 3, wherein said temperature is −9° C.

5. The process of claim 2, wherein said compound is benzaldehyde, said solvent is N-methylpyrrolidinone, said base is potassium hydroxide and said alkanol methanol at temperature ranging from −15° C. to 0° C.

6. The process of claim 5, wherein the temperature is −5° C.

7. The process of claim 2, wherein said compound is 3-nitrobenzaldehyde, said solvent is N-methylpyrrolidinone, said base is potassium hydroxide and said alkanol is methanol at temperatures ranging from −15° C. to 0° C.

8. The process of claim 7, wherein said temperature is −5° C.

9. The process of claim 2, wherein said compound in anisaldehyde, said solvent is N-ethylpyrrolidinone, said base is potassium t-butoxide and said alkanol is methanol at temperatures ranging from −15° C. to 0° C.

10. The process of claim 9, wherein the temperature is −10° C.

11. The process of claim 3, wherein said alkanol is ethanol or isopropanol.

12. The process of claim 11, wherein said alkanol is isopropanol.

* * * * *